United States Patent [19]

Sloma

[11] Patent Number: 4,695,543
[45] Date of Patent: Sep. 22, 1987

[54] ALPHA INTERFERON GX-1

[75] Inventor: Alan Sloma, Silver Spring, Md.

[73] Assignee: Bristol-Myers Company, New York, N.Y.

[21] Appl. No.: 602,275

[22] Filed: Apr. 24, 1984

Related U.S. Application Data

[63] Continuation of Ser. No. 361,364, Mar. 23, 1982, abandoned.

[51] Int. Cl.[4] .................. C12P 21/02; C12P 21/00; C12P 21/04; C12P 19/34; C12N 15/00; C12N 1/00; C12N 1/20; C07H 21/04
[52] U.S. Cl. .................................... 435/70; 435/68; 435/71; 435/91; 435/172.3; 435/243; 435/253; 435/811; 435/317; 536/27; 935/11; 935/18; 935/29; 935/72; 935/73
[58] Field of Search .................. 435/68, 70, 91, 172.3, 435/253, 317, 811, 71, 243; 536/27; 935/11, 18, 19, 29, 72, 73

[56] References Cited

U.S. PATENT DOCUMENTS 4,456,748 6/1984 Goeddel et al. ...................... 536/27

FOREIGN PATENT DOCUMENTS 043980 1/1982 European Pat. Off. ......... 435/172.3
2079291 1/1980 United Kingdom .
1565190 4/1980 United Kingdom ............... 536/16.8

OTHER PUBLICATIONS

Maeda et al, "Construction and Identification of Bacterial Plasmids Containing Nucleotide Sequence for Human Leukocyte Interferon", Proc. Natl. Acad. Sci. USA 77: 7010 (1980).
Science, vol. 212, 1159, Jun. 5, 1981 R. M. Lawn et al.
Nature, vol. 287, no. 4781, 408, Oct. 1980, Allen et al.
Goeddel, D. V., et al. Nature 287 (5781): 411–416 (1980); 209:20-26 (1981).

Brack, C. et al., Gene 15:379–394 (1981).
Nagata, S., et al. Nature 284:316-20 (1980).
Streuli, M., et al. Science 209:1343-47 (1980).
Goeddel, D. V., et al., Nucleic Acids Research 8:4057-4074.
Taniguichi, T., et al., Nature 285:547-49 (1980).
Taniguichi, T. et al., Proc. Natl. Acad. Sci. USA 77:5230-5233.

Primary Examiner—James Martinell
Attorney, Agent, or Firm—Bernard, Rothwell & Brown

[57] ABSTRACT

A cloned human alpha-interferon Gx-1 gene, plasmids containing the human alpha-interferon Gx-1 gene, and microorganisms transformed by those plasmids are disclosed. Also disclosed is the polypeptide, alpha-interferon Gx-1.

19 Claims, 2 Drawing Figures

```
C A G A A A A C C T A C C C A A G G A G T G T T A C C C T C
              10            20              30
A T C A A C C A G C C C A G C A G C A T C T T C G G G A T
          40              50              60
                                        MET   MET
T C C C A A T G C A T T G C C C T T T G C T T T A A T G A T G
          70              80              90
ALA   LEU   VAL   VAL   LEU   SER   CYS   LYS   SER   SER
G C C C T G G T G G T G C T C A G C T G C A A G T C A A G C
          100             110             120
CYS   SER   LEU   GLY   CYS   ASN   LEU   SER   GLN   THR
T G C T C T C T G G G C T G T A A T C T G T C T C A A A C C
          130             140             150
HIS   SER   LEU   ASN   ASN   ARG   ARG   THR   LEU   MET
C A C A G C C T G A A T A A C A G G A G G A C T T T G A T G
          160             170             180
ILE   MET   ALA   GLN   MET   GLY   ARG   ILE   SER   PRO
A T A A T G G C A C A A A T G G G A A G A A T C T C T C C T
          190             200             210
PHE   SER   CYS   LEU   LYS   ASP   ARG   HIS   ASP   PHE
T T C T C C T G C C T G A A G G A C A G A C A T G A C T T T
          220             230             240
GLY   PHE   PRO   GLN   GLU   GLU   PHE   ASP   GLY   ASN
G G A T T T C C T C A G G A G G A G T T T G A T G G C A A C
          250             260             270
GLN   PHE   GLN   LYS   ALA   GLN   ALA   ILE   SER   VAL
C A G T T C C A G A A G G C T C A A G C C A T C T C T G T C
          280             290             300
LEU   HIS   GLU   MET   ILE   GLN   GLN   THR   PHE   ASN
C T C C A T G A G A T G A T C C A G C A G A C C T T C A A T
          310             320             330
LEU   PHE   SER   THR   LYS   ASP   SER   SER   ALA   THR
C T C T T C A G C A C A A A G G A C T C A T C T G C T A G T
          340             350             360
TRP   ASP   GLU   THR   LEU   LEU   ASP   LYS   PHE   TYR
T G G G A T G A G A C A C T T C T A G A C A A A T T C T A C
          370             380             390
```

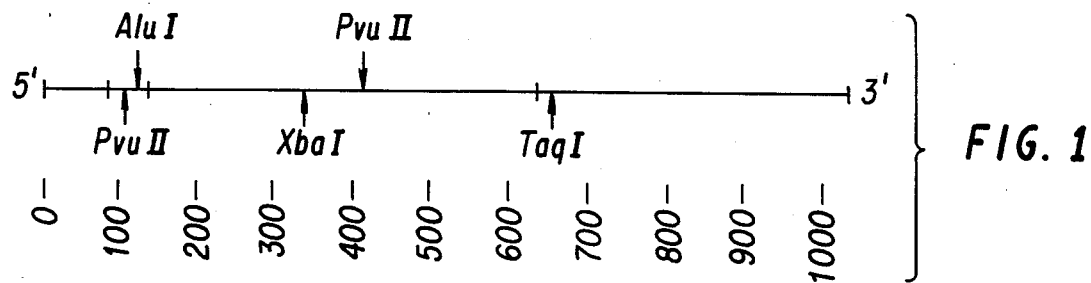

FIG. 1

```
C A G A A A A C C T A C C C A A G G A G T G T T A C C C C T C
                  10              20                    30
A T C A A C C A G C C C A G C A G C A T C T T C G G G A T
              40              50                    60
                                              MET  MET
T C C C A A T G C A T T G C C C T T T G C T T T A A T G A T G
              70              80                        90
 ALA  LEU  VAL  VAL  LEU  SER  CYS  LYS  SER  SER
G C C C T G G T G G T G C T C A G C T G C A A G T C A A G C
              100             110                   120
 CYS  SER  LEU  GLY  CYS  ASN  LEU  SER  GLN  THR
T G C T C T C T G G G C T G T A A T C T G T C T C A A A C C
              130             140                   150
 HIS  SER  LEU  ASN  ASN  ARG  ARG  THR  LEU  MET
C A C A G C C T G A A T A A C A G G A G G A C T T T G A T G
              160             170                   180
 ILE  MET  ALA  GLN  MET  GLY  ARG  ILE  SER  PRO
A T A A T G G C A C A A A T G G G A A G A A T C T C T C C T
              190             200                   210
 PHE  SER  CYS  LEU  LYS  ASP  ARG  HIS  ASP  PHE
T T C T C C T G C C T G A A G G A C A G A C A T G A C T T T
              220             230                   240
 GLY  PHE  PRO  GLN  GLU  GLU  PHE  ASP  GLY  ASN
G G A T T T C C T C A G G A G G A G T T T G A T G G C A A C
              250             260                   270
 GLN  PHE  GLN  LYS  ALA  GLN  ALA  ILE  SER  VAL
C A G T T C C A G A A G G C T C A A G C C A T C T C T G T C
              280             290                   300
 LEU  HIS  GLU  MET  ILE  GLN  GLN  THR  PHE  ASN
C T C C A T G A G A T G A T C C A G C A G A C C T T C A A T
              310             320                   330
 LEU  PHE  SER  THR  LYS  ASP  SER  SER  ALA  THR
C T C T T C A G C A C A A A G G A C T C A T C T G C T A G T
              340             350                   360
 TRP  ASP  GLU  THR  LEU  LEU  ASP  LYS  PHE  TYR
T G G G A T G A G A C A C T T C T A G A C A A A T T C T A C
              370             380                   390
```

FIG. 2A

```
THR GLU LEU TYR GLN GLN LEU ASN ASP LEU
A C T G A A C T T T A C C A G C A G C T G A A T G A C C T G
    400               410               420
GLU ALA CYS MET MET GLN GLU VAL GLY VAL
G A A G C C T G T A T G A T G C A G G A G G T T G G A G T G
    430               440               450
GLU ASP THR PRO LEU MET ASN VAL ASP SER
G A A G A C A C T C C T C T G A T G A A T G T G G A C T C T
    460               470               480
ILE LEU THR VAL ARG LYS TYR PHE GLN ARG
A T C C T G A C T G T G A G A A A A T A C T T T C A A A G A
    490               500               510
ILE THR LEU TYR LEU THR GLU LYS LYS TYR
A T C A C C C T C T A T C T G A C A G A G A A G A A A T A C
    520               530               540
SER PRO CYS ALA TRP GLU VAL VAL ARG ALA
A G C C C T T G T G C A T G G G A G G T T G T C A G A G C A
    550               560               570
GLU ILE MET ARG SER PHE SER LEU SER ALA
G A A A T C A T G A G A T C C T T C T C T T T A T C A G C A
    580               590               600
ASN LEU GLN GLU ARG LEU ARG ARG LYS GLU
A A C T T G C A A G A A A G A T T A A G G A G G A A G G A A
    610               620               630
T G A A A A C T G G T T C A A C A T C G A A A T G A T T C
            640               650               660
T C A T T G A C T A G T A C A C C A T T T C A C A C T T C T T
            670               680               690
G A G T T C T G C C G T T T C A A A T A T T A A T T T C T
            700               710               720
G C T A T A T C C A T G A C T T G A G T T G A A T C A A A A T
            730               740               750
T T T C A A A C G T T T C A C A C G T G T T A A G C A A C
            760               770               780
A C T T C T T T A G C T C C A C A G G G A C A A A A T C T T T
            790               800               810
A C A G A T G A T C A T G C C A A T C T A T C T A T T C T
            820               830               840
A T C T A T T T A T C T A T C T G T C T G T C T T C T A T C T
            850               860               870
A A T C T A T T T A A A T A T T T A T T T A T T T A T A A
            880               890               900
G A T T T A A A T T A T T T T A A A C T T A T G T T T G T T C
            910               920               930
A G G T A A T A T T A C A T C C A C C T T T A C T T T G T
            940               950               960
G G C T A A T A T A A T A A A A T A T G T T C T T T A T G T T
            970               980               990
T T G T C A A G C T G A T T A T T T T G C T T T G T T A C
            1000              1010              1020
T T A G A T T T T T A G
            1030
```

FIG. 2B

ALPHA INTERFERON GX-1

This is a continuation of application Ser. No. 361,364 filed Mar. 23, 1982 now abandoned.

The present invention relates to a cloned human gene, which specifies the biosynthesis of interferon. More particularly, the invention relates to a cloned human gene which specifies the biosynthesis of *alpha-interferon Gx-1*; to a plasmid containing such gene; to a microorganism transformed with such a plasmid; and to a polypeptide designated alpha-interferon Gx-1.

The term "interferon" describes a family of animal proteins which possess antiviral and other potentially useful activities. Interferon is produced in vivo in minute amounts, in response to viral infections. Relatively small amounts of human interferons for research and clinical studies have been recovered from tissue cultures of human cells, which have been induced to make interferon by viruses or other inducing agents. These techniques are quite expensive, and the amounts of interferon which can be so produced are limited. Accordingly, there has been considerable interest in developing genetically engineered microorganisms, that are capable of efficiently producing interferon. The cloning of certain human interferon genes and the bacterial expression of interferon have been reported. Nagata, S. et al. *Nature*, 284, 316–320 (1980); Goeddel, D., et al. *Nature*, 287, 411–416 (1980); Streuli, M., Nagata, S., and Weissmann, C., *Science*, 209, 1343–1347 (1980); Derynck, R., et al., *Nucleic Acid Research*, 8, 4057–4074 (1980); and Taniguichi, T., et al., *Proc. Natl. Acad. Sci. USA*, 77 5230–5233 (1980).

Interferons are presently classified into the following three categories: leukocyte or alpha-interferon, fibroblast or beta-interferon, and immune or gamma-interferon. Current scientific evidence suggests that there are perhaps ten to fifteen distinct alpha-interferons and only one form of beta-interferon. Goeddel, D.V., et al., *Nature*, 290, 20–26 (1981). Brack, C., et al., Gene, 15, 379–394 (1981). Several of the alpha-interferon genes have been cloned, and their nucleotide sequences published. Goedell, et al. *Nature*, 290, supra. Heretofore, the isolation or cloning of the full-length alpha-interferon gene designated alpha-interferon G by prior investigators has not been reported, and only a portion of its nucleotide sequence has been disclosed. The bacterial production of the intact human alpha-interferon G protein has not been reported.

In accordance with the present invention, a novel human alpha-interferon gene, which is designated herein as alpha-interferon Gx-1, has been cloned, and characterized, and bacterial expression of the gene is described. The nucleotide sequence of the full length alpha-interferon Gx-1 gene and the amino acid sequence of the polypeptide specified by that gene are also reported herein. A portion of the nucleotide sequence reported here corresponds with the partial nucleotide sequence previously reported for alpha-interferon G, and it is therefore possible that the gene portion previously obtained and sequenced was a fragment of the gene here designated alpha-interferon Gx-1.

The obtention of the alpha-interferon Gx-1 gene, its amplification in vivo, and its expression in a microbial culture have, except where otherwise indicated, been accomplished utilizing conventional techniques of molecular biology. E.g., see, Ullrich, A. et al., *Science*, 196, 1313 (1977) and Seeburg, P.H., et al., *Nature*, 270, 486 (1977).

The procedures leading to an alpha-interferon Gx-1-producing microorganism can be divided into the following six major stages, each of which is described more fully herein: (1) in vitro induction of human leukocytes to produce alpha-interferon Gx-1 messenger RNA (mRNA), (2) recovery and isolation of alpha-interferon Gx-1 mRNA, (3) in vitro synthesis of complementary DNA (cDNA), using the alpha-interferon Gx-1 mRNA as a template, (4) insertion of the cDNA into a suitable cloning vector and transformation of microbial cells with that cloning vector, (5) selection of microbial clones containing the alpha-interferon-Gx-1 gene, and (6) insertion of the cloned gene into a suitable expression vector and transformation of a suitable host microorganism with that expression vector.

Alha-interferons are produced by virus-treated leukocytes, and, although genes which specify alpha-interferons are present in the chromosomes of every cell in the body, for reasons discussed below, genes associated with alpha-interferons are most readily obtained from such virus-treated leukocytes.

Eukaryotic genes are contained in the chromosomal DNA of the cell nuclei. This chromosomal DNA exists in a compact nucleoprotein complex called chromatin. Isolating a particular gene from eucaryotic chromosmoal DNA is a tedious and often unfeasible approach. On the other hand, messenger RNA (mRNA), having a ribonucleotide sequence corresponding to the gene of interest, can conveniently be recovered from eucaryotic cells that are producing the protein specified by the gene. Therefore, the mRNA usually provides the desired genetic information in its most accessible form.

Alpha-interferon mRNA may be recovered in useful quantities from leukocytes which have been treated with a virus or other inducing agent. Generally, the procedure described by Contell, K., et al., *In Vitro*, Waymouth Ed., pp. 35–38, The Tissue Culture Association, Rockville, MD (1974), has been used to induce leukocytes to produce alpha-interferon mRNA. This procedure involves suspending red cell-free leukocytes (e.g., obtained by fractionating human blood) in a suitable nutrient medium and infecting with a suitable inducing agent, preferably a virus, such as Newcastle Disease Virus and incubating until sufficient interferon activity is obtained. Interferon activity may be determined by a viral inhibition test, such as that described by Rubinstein, Familetti, Pestka, *J. Virol*, 37, 755–758 (1981). Induced leukocytes are advantageously washed and frozen prior to recovery of the mRNA.

The alpha-interferon Gx-1 mRNA produced by the induced cells is complementary to one of the two strands of the alpha-interferon Gx-1 gene, and may be employed as a template for the synthesis of complementary DNA (cDNA) as hereinafter described. To effectively utilize the mRNA for the synthesis of cDNA, it is advantageously recovered from the induced cells in relatively pure form. This recovery involves separating the mRNA not only from the cell membranes, proteins, lipids, carbohydrates, salts, and such, present in the cells, but also from mRNA molecules associated with the biosynthesis of proteins other than the desired *alpha-* interferon. The procedures described by Chirgwin, J.M., et al. *Biochemistry*, 18, 5294–5299 (1979) and McCandliss, R., Sloma, R., and Pestka S., *Methods of Enzymology*, Vol. 70 (1981), may be used advantageously for the recovery of alpha-interferon Gx-1 mRNA. RNA is inherently less stable than DNA, and is particularly subject to degradation by ribonucleases that are present in relatively high concentrations in human leukocytes. Therefore, the mRNA recovery procedures generally employ means for rapidly inactivating any ribonucleases which are present.

In general, recovery of total RNA, is initiated by disrupting the cells in the presence of a ribonuclease-inactivating substance. Disruption of the cells may be accomplished by subjecting the cells to a lysing reagent, freezing/thawing, or mechanical disruption; preferably a combination thereof. A mixture of guanidine thiocyanate and a reducing agent, such as mercaptoethanol, has been found to function effectively as a lysing agent and a ribonuclease inactivator.

After disruption of the cells, the solid cell debris is removed, e.g. by centrifugation, and the RNA is precipitated from the resulting clarified solution. Precipitation is effeted, by known techniques, such as adding a water-miscible alcohol, e.g. ethanol to the solution, in a precipitating amount. The solution is advantageously maintained at a low temperature, e.g., less than about 0° C during these procedures, to facilitate RNA precipitation.

The alpha-interferon Gx-1 mRNA may be isolated from the precipitated RNA by any of several known techniques, or combinations thereof, e.g., see Adams, R.L.P., et al., Davidson's *The Biochemistry of the Nucleic Acids*, 8th Ed., pp. 52-58, Academic Press, Inc., N.Y. (1976). Density gradient centrifugation using a cesium chloride gradient, followed by phenol extraction can be used as a preliminary isolation technique. Glisin, et al., *Biochemistry*, 13, 2633 (1974).

Affinity chromatography can be used to further purify alpha-interferon mRNA. Alpha-interferon mRNA is polyadenylated; therefore, it can readily be separated from non-adenylated RNA by chromatography on an oligo (dT)-cellulose column. Green, M., et al., *Arch. Biochem. Biophys.*, 172, 74 (1976).

As a final purification step, the mRNA can be fractionated by centrifugation through a sucrose gradient. Alpha-Interferon mRNA, migrating as about a 12S species, may be isolated by this procedure.

Cell-free translation of the final purified mRNA (and intermediate fractions if desired) can be employed to confirm that alpha-interferon mRNA has been obtained. A number of cell-free translational systems have been devised, such as wheat germ extract (Martial, J. et al., *Proc. Nat. Acad. Sci. USA*, 74, 1816 (1977), an mRNA-dependent reticulocyte lysate (Pelham, H.R.B., et al., *Eur. J. Biochex'.*, 67, 247 (1976), and oocytes from *Xenopus laevis* (Sloma, A., McCandliss, R. and Peska, S., *Methods in Enzymology*, Vol. 70 (1981). Translation of the recovered and isolated alpha-interferon G mRNA is preferably conducted in the *X.laevis* oocyte system.

Translation in this system is accomplished by suspending oocytes obtained from healthy frogs in a suitable incubation medium, e.g. see Cavalieri, et al., *Proc. Natl. Acad. Sci. USA.*, 74, 3287, (1977). A sterile water solution of the mRNA is injected into about ten oocytes using a micromanipulation device. The injected oocytes are incubated and then analyzed for interferon activity. The oocytes are analyzed by homogenizing them in their incubation medium, and centrifuging to remove the insoluble membranes, proteins and the like. An aliquot of the supernatant is then analyzed for interferon by its ability to protect human fibroblasts from cytopathic effects caused by Vesicular Stomatitis Virus, see Rubinstein, et al., supra. The mRNA obtained by the foregoing procedures has been found to produce interferon titers of about 2000-5000 units per milliliter (u/ml) in the *X.laevis* oocyte translational system.

The mRNA fractions having the highest activity by the *X.laevis* oocyte test can be combined to provide a template for cDNA synthesis. This procedure involves enzymatically constructing double-stranded DNA, which has a nucleotide base pair sequence identical to the functional sequence of the original chromosomal gene. The cDNA does not contain any noninformational segments (introns) which might be present on the eukaryotic gene, and thus can ultimately be transcribed and translated in prokaryotic systems.

Synthesis of cDNA employs avian myeloblastosis virus reverse transcriptase. This enzyme catalyzes the synthesis of a single strand of DNA from deoxynucleoside triphosphates on the mRNA template. Kacian, D. L., et al., *Proc. Nat'l Acad. Sci. USA*, 73, 2191 (1976). The poly r(A) tail of mRNA permits oligo (dT) (of about 12-18 nucleotides) to be used as a primer for cDNA synthesis. The use of a radioactively-labelled deoxynucleoside triphosphate facilitates monitoring of the synthesis reaction. Generally, a $^{32}$P-containing deoxynucleoside 0 35 triphosphate, such as [$\alpha$-$^{32}$P]dCTP may be used advantageously for this purpose. The cDNA synthesis is generally conducted by combining the mRNA, the deoxynucleoside triphosphates, the oligo (dT) and the reverse transcriptase in a properly buffered solution. The solution also preferably contains small amounts of actinomycin D and dithiothreitol to promote full length synthesis, Kacian, D. L., et al. supra. This solution is incubated at an elevated temperature, e.g., about 40°-50° C., for a time sufficient to allow formation of the cDNA copy, e.g. about 5-20 minutes. The conditions of the reaction are essentially as described by Kacian, D. L., et al., supra. After incubation, ethylenediaminetetraacetic acid is added to the solution, and the solution extracted with phenol:chloroform (1:1 by vol.). The aqueous phase is advantageously purified by gel filtration chromatography, and the cDNA-mRNA complex in the eluate is precipitated with alcohol.

The mRNA can be selectively hydrolyzed in the presence of the cDNA with dilute sodium hydroxide (about 0.1 M) at an elevated temperature, e.g., about 60°-80° C. for about 15-30 minutes. Neutralization of the alkaline solution and alcohol precipitation yields a single-stranded cDNA copy.

The single-stranded cDNA copy has been shown to have a 5'-poly (dT) tail, and to have a 3'terminal hairpin structure, which provides a short segment of duplex DNA. Efstratiadis, A., et al., *Cell*, 7, 279 (1976). This 3'hairpin structure can act as a primer for the synthesis of a complementary DNA strand. Synthesis of this complementary strand is conducted under essentially the same conditions as the synthesis of the cDNA copy, except that the Klenow fragment of DNA polymerase I (Klenow, H., et al., *Eur. J. Biochem.*, 22, 371 (1971)) is substituted for reverse transcriptase. The duplex cDNA recovered by this procedure has a 3'loop, resulting from the 3'hairpin structure of the single-stranded cDNA copy. This 3'loop can be cleaved by digestion with the enzyme, S1 nuclease, using essentially the procedure of Ullrich, A., et al., supra. The S1 nuclease digest may be extracted with phenol-chloroform, and the resulting cDNA precipitated from the aqueous phase with alcohol.

The intact double-stranded DNA, corresponding to an alpha-interferon gene may be isolated by polyacrylamide gel electrophoresis, using essentially the procedure of Maniatis, et al., *Biochemistry*, 14, 3787 (1975). After staining the gel, e.g., with ethidium bromide to visualize restriction enzyme digests incorporated as molecular weight markers, a photographic film is exposed with the gel to locate the radioactively labelled double-stranded cDNA gene. The region of the gel containing DNA molecules between 500 and 1300 base pairs long is removed, and the DNA is eluted electrophoretically, essentially by the method of Smith, H. O., *Methods of Enzymology*, 65, 371 (1980). DNA corresponding in size to the alpha-interferon Gx-1 gene (ca. 900 base pairs) is recovered by phenol-chloroform extraction of the electrophoretic eluate, followed by alcohol precipitation of the cDNA from the aqeuous phase.

For purposes of amplification and selection, the double stranded cDNA gene prepared as described above is generally inserted into a suitable cloning vector, which is used for transforming appropriate host cells. Suitable cloning vectors include various plasmids and phages, and plasmids are generally preferred. The criteria for selecting a cloning vector include its size, its capability for replicating in the host cells, the presence of selectable genes, and the presence of a site for insertion of the gene. With respect to its size, the vector is advantageously relatively small, to permit large gene insertions, and so as not to divert large amounts of cellular nutrients and energy to the production of unwanted macromolecules. The vector also includes an intact replicon which remains functional after insertion of the gene. This replicon preferably directs the desired mode of replication of the plasmid, i.e., multiple copies or a single copy per cell, or a controllable number of copies per cell. Genes specifying one or more phenotypic properties, preferably antibiotic resistance, facilitate selection of transformants. The insertion site is advantageously a unique restriction site for a restriction endonuclease. A cloning vector meeting all of these criteria is the plasmid pBR322. Bolivar, F., et al. *Gene*, 2, 95 (1977). This plasmid is small (about $2.8 \times 10^6$ daltons), carries genes for ampicillin (amp) and tetracycline (tet) resistance, and is subject to relaxed replication in *E.coli*. The plasmid also has a restriction site for the endonuclease, *PstI*, which occurs within the amp gene. The cDNA can be conveniently inserted into this plasmid by a homopolymeric tailing technique. Nelson, T., et al., *Methods of Enzymology*, 68, 41 (1980). Homopolymer tails, e.g., poly-dC, are added to the 3'-hydroxyls of the interferon double-stranded cDNA gene, by reaction with the appropriate deoxynucleoside triphosphate, e.g., dCTP, in the presence of terminal deoxynucleotidyl transferase (Chang, L. M. S., et al., *J. Biol. Chem.*, 246, 909 (1971)). The plasmid is opened by digestion with the appropriate endonuclease, and complementary homopolymer tails, e.g., poly dG, are added to the 3'-hydroxyls of the opened plasmid, using the identical homopolymer tailing technique e.g., using dGTP. If desired, the tailing reactions may be monitored, by employing radioactively labelled deoxynucleotide triphosphates e.g., [$^3$H]dCTP and [3H]dGTP, in the reactions. Generally, the reactions are conducted to provide tails about 10–20 nucleotides long. The tailed cDNA and plasmid are recovered, e.g., by phenol extraction followed by alcohol precipitation. The two "tailed" DNA species are annealed by incubating a buffered solution of equimolar concentrations of the two species, to yield a recombinant plasmid containing the alpha-interferon Gx-1 gene.

A suitable $amp^S$, $tet^S$ strain of *E.coli* may be transformed with the recombinant plasmid, using essentially the method of Lederberg, *J. Bacteriology*, 119, 1072 (1974). Transformants are typically grown on a standard L-broth, containing about 50 ug/ml of tetracyline. Samples of colonies growing on the tetracycline-containing medium are then transferred to a second medium containing about 50 ug/ml of ampicillin. Because the pBR322 plasmid imparts tetracycline resistance to the cells, colonies growing on the tetracycline-containing medium must contain that plasmid. On the other hand, the ampicillin resistance of the pBR322 plasmid is destroyed by insertion of the gene, therefore, only $tet^R$, $amp^S$ colonies are selected for further analysis.

Generally, several hundred to several thousand potential alpha-interferon Gx-1 clones are produced by these procedures. To identify those colonies which contain the alpha-interferon Gx-1 gene, a radioactively labelled DNA probe may advantageously be employed. Grunstein, M, et al., *Proc. Nat'l. Aca. Sci. USA*, 72, 3961–3965 (1975). A particularly preferred DNA probe is the tridecadeoxyribonucleotide probe described in copending U.S. patent application Ser. No. 286,351, herein incorporated by reference. That probe contains a thirteen-nucleotide sequence, which is complementary to a sequence common to known human leukocyte and human fibroblast interferon genes. To use the probe, DNA from each colony (or from groups of colonies) is fixed to discrete zones of a nitrocellulose filter and denatured. A solution of the probe is applied thereto under hybridizing conditions. Unhybridized probe is washed from the filter, and colonies containing DNA to which the probe hybridized are identified by autoradiography.

Positive clones may be cultivated on suitable growth media to obtain ample quantities of cells from which to extract the plasmid DNA. The plasmid DNA is extracted, using conventional techniques, such as disruption of the cells, followed by phenol extraction, and alcohol precipitation. The DNA may be separated, e.g. by electrophoresis or sucrose gradient sedimentation. Plasmid DNA containing inserts about 900 base pairs is selected for further characterization.

Because the techniques used for inserting the cDNA into the cloning vector reforms two restriction endonuclease sites corresponding to the original vector insertion site, the cloned gene may conveniently be excised from the plasmid DNA by digestion with the appropriate endonuclease. The excised gene is then characterized by restriction mapping and sequencing analysis. The restriction map of the excised alpha-interferon Gx-1 gene of the present invention is shown in FIG. 1 of the drawings. The isolated gene consists of 1032 base pairs. The gene has noncoding regions at the 5' end (base pairs 1–85) and at the 3' end (base pairs 632–1032). The 5' end of the coding region (86–133 base pairs) includes a leader, and the mature alpha-interferon Gx-1 protein is specified by the region from base pair number 134 to base pair number 631.

The nucleotide sequence of this gene was determined by the method of Sanger, et al. *Proc. Nat'l Acad. Sci. USA*, 74, 5463–5467 (1977), and this nucleotide sequence is shown in FIG. 2 of the drawings. The drawing shows the 5'—>3 strand of the noncoding and coding regions, along with the amino acid sequence specified by the gene. As used in FIG. 2 and elsewhere herein, the abbreviations have the following standard meanings:

A = deoxyadenyl
T = thymidyl
G = deoxyguanyl
C = deoxycytosyl
GLY = glycine
ALA = alanine
VAL = valine
LEU = leucine
ILE = isoleucine
SER = serine
THR = threonine
PHE = phenylalanine
TYR = tyrosine
TRP = tryptophan
CYS = cysteine
MET = methionine
ASP = aspartic acid
GLU = glutamic acid
LYS = lysine
ARG = arginine
HIS = histidine
PRO = proline
GLN = glutamine
ASN = asparagine It will be appreciated that because of the degeneracy of the genetic code, the nucleotide sequence of the gene can vary substantially. For example, portions or all of the gene could be chemically synthesized to yield DNA having a different nucleotide sequence than that shown in FIG. 2, yet the amino acid sequence would be preserved, provided that the proper codon-amino acid assignments were observed. Having established the nucleotide sequence of the alpha-interferon Gx-1 gene and the amino acid sequence of the protein, the gene of present invention is not limited to a particular nucleotide sequence, but includes all variations thereof as permitted by the genetic code.

A culture of E.coli cells containing the cloned alpha-interferon Gx-1 gene was analyzed for interferon activity by the viral inhibition method of Rubinstein, et al. supra, the cells were found to produce small amounts of interferon activity. This cell culture has been designated A3-26, and has been deposited with the American Type Culture Collection, Rockville, MD as ATCC No. 39063.

Having obtained the cloned alpha-interferon Gx-1 gene, that gene may then be introduced into microorganisms under conditions designed to achieve high levels of protein expression. To accomplish this goal, the gene can advantageously be inserted into an expression vector. Like cloning vectors, expression vectors may be plasmids or phages; plasmids being preferred. In addition to the criteria for a good cloning vector, an expression vector also contains properly positioned control signals which direct transcription and translation of the cloned gene. Guarante, L. et al., Cell, 20 543-553 (1980). Typically, a gene is inserted into an intact operon of a plasmid, and expression of the gene is controlled by that operon. The lactose (lac) and tryptophan (trp) operons of E.coli have been used for this purpose. Roberts, T. M., et al., Proc. Nat'l Acad. Sci. USA, 76, 760-764 (1979).

The present invention has been described in connection with the use of E.coli as the bacterial host for recombinant DNA containing the alpha-interferon Gx-1 gene, but skilled molecular biologists will appreciate that other gram-negative bacteria, such as Pseudomonas; gram-positive bacteria, such as Bacillus; and higher unicellular organisms, such as yeasts and fungi can be employed for cloning and/or expression of the alpha-interferon Gx-1 gene.

The invention is further illustrated by reference to the following examples, which are not intended to be limiting.

EXAMPLE I

Induction of Leukocytes

The starting material for the induction procedures was a residue from a plateletpheresis preparation. Each residue contained the white cells from 6 to 20 units of human blood admixed with contaminating red cells. Two residues were pooled and centrifuged in a bottle for 7 minutes at $1600 \times g$. Most of the red cells were removed from the bottom of the bottle with a pipet. The remaining volume was measured, and remaining red cells were lysed by rapid addition of ten volumes of 0.83% ammonium chloride. After 10 minutes at 4° C., the white cells were collected by centrifugation and suspended in 500 ml of Eagle's minimum essential medium (without phosphate buffer) supplemented with 10% heat-inactivated calf serum, 3 mg/ml of tricine and 25 ug/ml of neomycin. This gave a cell concentration of about $10^7$ cells/ml. Newcastle Disease Virus (NDV), strain B1, was added to the cell suspension at a final concentration of 100 hemagglutinin units per ml, and the cells were incubated with agitation at 37° C. After 5 hours, 40 ml of the culture was transferred to a smaller agitated vessel which was incubated for another 18 hours at 37° C. The cells of this aliquot were then removed by centrifugation, and the supernatant was assayed for interferon by its ability to protect human fibroblasts from cytopathic effects caused by Vesicular Stomatitis Virus. The titer was 25,000 IU/ml. The remaining 450 ml of the culture (5 hr after addition of NDV) was centrifuged. The supernatant was assayed for interferon. The titer was 6400 IU/ml. The cell pellet was washed with PBS (8.2 g/L sodium chloride, 0.22 g/L potassium chloride, 0.20 g/L monobasic potassium phosphate, 1.14 g/L dibasic sodium phosphate), and the washed pellet, weighing 4.9 grams, was frozen at −70° C.

EXAMPLE II

Extraction of mRNA from Induced Leukocytes

The following solutions were Prepared:
Solution A: The lysis solution contained 4M reagent grade guanidine thiocyanate, 0.1M Tris-HCl, pH 7.5, and 0.1M 2-mercaptoethanol. Guanidine thiocyanate (472.6 g) was dissolved with heating in 500 ml of water and 200 ml of Tris buffer stock solution (0.5M Tris-HCl, pH 7.5). The solution was allowed to cool to room temperature after which 7.15 ml of 2-mercaptoethanol were added, and the solution was diluted to 1,000 ml with sterile water. Particulate matter from the guanidine thiocyanate was removed by filtration through a Nalge disposable filter unit. The solution was stable for at least one month at room temperature. Strong precautions should be taken to avoid contact of this reagent with skin.

The lysis of induced cells was performed in a fume hood. The cells from Example I were partially broken while kept frozen.

Solution B: The wash solution contained in 6M ultrapure guanidine hydrochloride, 10 mM Na$_2$EDTA, pH 7.0, and 10 mM dithiothreitol. Because of the high purity of the guanidine hydrochloride used, no filtration of this solution was necessary, and it was stable when stored at room temperature. Again, care should be taken to avoid contact of this solution with the skin.

The lysis of induced cells was performed in a fume hood. The cells from Example I were partially broken while kept frozen and placed in 20 ml of Solution A per gram (wet weight) of cells in the chamber of a high speed homogenizer. The homogenizer was operated at full speed for 2 minutes to lyse the cells. The lysate is then centrifuged for 10 minutes at 12,000 rpm in a Sorvall GSA rotor to remove any debris present.

The supernatant containing the RNA and other cellular components was acidified at pH 5 by addition of 0.04 volume of 1N acetic acid, and the RNA was precipitated by adding 0.5 volume of absolute ethanol. After mixing, the solution was kept at $-20°$ C. for at least 2 hours. Leaving the mixture at $-20°$ C. for much longer periods does not significantly increase the yield of RNA and results in the coprecipitation of larger amounts of protein, which may be difficult to redissolve in the next step. The precipitated RNA was collected by centrifugation for 10 min at 8,000 rpm in a Sorvall GSA rotor. The supernatant was removed and the pellet was dissolved in approximately 0.5 volume (relative to the original volume of the lysate) of Solution B at 70° C. The RNA was again acidified to pH 5 by addition of 0.04 volume of 1N acetic acid. The solution was cooled in an ice bath, and the RNA was precipitated with 0.5 volume of cold ethanol. Precipitation was almost immediate and quantitative. The RNA was collected by centrifugation at 6,000 rpm for 10 min in a Sorvall GSA rotor. The procedure with Solution B was then repeated once, with a further reduction in volume. The final pellet was dissolved in sterile 0.24M sodium acetate, pH 5.5, and precipitated by addition of 2.5 volumes of ethanol. The total RNA was stored as the ethanol precipitate at $-20°$ C. until further use. The RNA at this stage was undegraded and free of proteins and DNA.

The first step in purifying the interferon mRNA involved affinity chromatography on an oligo (dT)-cellulose column, using the method of Green, M., et al., *Arch. Biochem. Biophys.*, 172, 74 (1976). The RNA solution (30–50 A$_{260}$ units/ml) was adjusted to 0.5M NaCl by addition of 0.11 volume of 5M NaCl and then applied to a column containing 5 g of oligo (dT)-cellulose (T-3, Collaborative Research) equilibrated with 10 mM Tris-HCl, pH 7.4, and 0.5M NaCl at a flow rate of about 20 ml/hour. Non-bound RNA was removed from the column by washing with the same buffer until the optical density was less than 0.08 A$_{260}$ unit/ml. Poly(A) RNA was then eluted with 10 mM Tris-HCl, pH 7.4. The poly(A) was recycled over the column once more to decrease contamination by ribosomal and other non-poly(A) RNA's. After the first oligo(dT)-cellulose column chromatography, the RNA preparation was assayed for interferon mRNA activity by injection into *Xenopus laevis* oocytes as hereinafter described.

The interferon mRNA so obtained was enriched by sucrose gradient centrifugation. Linear gradients were prepared by mixing equal volumes of 5% (w/v) and 20% sucrose in 0.02M sodium acetate, pH 5, in the chambers of a Buchler gradient maker. After formation, the gradients were equilibrated at 4° C. for at least 4 hours. Prior to loading, the RNA samples were heated to 80° C. for 2 min and cooled rapidly in an ice bath to reduce aggregation. The samples were layered over the gradients and were centrifuged for 20 hours at 30,000 rpm at 4° C. using an SW40 rotor (Beckman). Following centrifugation, the gradients were collected by use of an Isco Gradient Pump modified such that a flow cell is attached to a Gilford spectrophotometer. The gradients were analyzed by pumping 50 % sucrose into the bottom of the tube. Fractions were collected, ethanol precipitated, dissolved in sterile water and assayed by injection into *Xenopus laevis* oocytes as hereinafter described. Leukocyte interferon mRNAs migrated approximately as 12 S species.

EXAMPLE III

Translation of Interferon mRNA in Xenous Laevis Oocytes

*Xenopus laevis* were obtained from Nasco, Ft. Atkinson, WI (#LM531LQ). The oocytes obtained from these frogs have been found to yield reproducible high titers of interferon. After the animal was placed in ice water for 30 min, it was sacrificed and the oocytes were removed and immediately placed in 150 ml of the following oocyte incubation media.

| Oocyte Incubation Media | |
|---|---|
| NaCl | 88 mM |
| KCl | 1 mM |
| NaHCO$_3$ | 2.4 mM |
| MgSO$_4$.7H$_2$O | 0.82 mM |
| Ca(NO$_3$)$_2$.4H$_2$O | 0.33 mM |
| CaCl$_2$.2H$_2$O | 0.41 mM |
| Tris base | 7.5 mM |
| Penicillin G, potassium | 18 units/ml (11 ug/ml) |
| Streptomycin | 18 ug/ml |

The final pH was adjusted to pH 7.6 with HCl and the solution was sterilized by filtration.

Individual oocytes were obtained by gently teasing apart the oocyte sacs with a blunt probe. The oocytes have a distinct animal and vegetal pole. The yolk of the vegetal pole has a light white-green color and the animal pole is black. Although they vary in size, most oocytes were approximately 1 mm in diameter. The largest oocytes, approximately 1.2–1.5 mm in diameter, tend to leak after injection and were not used. After isolation, the oocytes were stored at 5° C. Oocytes are capable of giving maximum interferon titer after 4–5 days storage at 5° C.

Interferon mRNA from Example II was dissolved in sterile water at a concentration of 0.5–1 mg/ml, and the solution was kept on ice until injected.

Injection needles were prepared by pulling five ul microdispenser tubes (#105G, Drummond Scientific) with a vertical pipette puller (Model 700B, David Kopf Instruments, Tujunga, CA). The pulled needles were sealed at the tip. The tips were then broken off with fine scissors under a dissecting microscope to form the needle with a tip of 0.005–0.01 mm in diameter. The microdispenser capillaries consisted of uniform bore tubing with 0.27 mm equivalent to 50 nl (5.4 mm equivalent to 1 ul).

To inject the RNA into the oocytes, two ul of interferon mRNA were placed in the bottom of a 60×15 mm round Petri dish filled with sterile mineral oil. The small aqueous bubble remained at the bottom against the wall of the dish. The injection needle was then clamped to the end of a Brinkman micromanipulator (#06-15-00) and attached to tubing which was connected to a hydraulic pressure system. Positive pressure fills the needle up to 2 mm from the open tip. The needle was then placed through the mineral oil into the solution of mRNA. The solution was drawn into the tube by capillary action, with the help of negative pressure applied to the system. The sample filled $\frac{1}{2}$-$\frac{3}{4}$ of the injection needle. A small air bubble remained between the RNA solution and the hydraulic fluid (sterile H2O). A small piece of graph paper with 1-mm divisions was placed on the needle and aligned with the meniscus.

For injection, ten oocytes were aligned against the edge of a slide taped to a square (100×100 mm) petri dish. The animal or vegetal pole can be injected without affecting the final interferon titer. As the needle entered the oocyte at a 60° angle, positive pressure was applied to the system. Displacement of the meniscus was approximately 0.3 mm for each oocyte injected, which is equivalent to about 50 nl injected per oocyte. The needle was removed from the oocyte and the remaining 9 were injected in sequence. About 40-50 ng of interferon mRNA were injected per oocyte. It has been previously shown that this concentration is saturating. Immediately after injection, the ten oocytes were placed in 0.1 ml of fresh oocyte incubation media and incubated for 18 h at 23° C. in a 1.5 ml sterile polypropylene conical tube.

After incubation, the oocytes were homogenized manually in the same tube in which they were incubated. This is important because some interferon is secreted into the incubation media. The extract was then centrifuged for 5 minutes in an Eppendorf centrifuge. Ninety ul of supernatant was carefully removed. A lipid layer formed at the top, which is toxic to the cells in the interferon assay. Therefore, as little of the lipid was removed as possible. The 90 ul of supernatant were then centrifuged again for 5 min. The supernatant was then assayed for interferon activity by the method of Rubinstein, et al. (supra). The interferon titer of the solution was 1260 U/ml.

EXAMPLE IV

Preparation of cDNA from mRNA

The following stock solutions and materials were prepared:
0.5M Tris-HCl, pH 8.3
1.4M KCl
0.25M MgC$_{12}$
0.05M dATP, pH 7.0
0.05M dCTP, pH 7.0
0.05M TTP, pH 7.0
[$^{32}$P]dCTP, 400 Ci/mmol, 1 mCi/ml (Amersham)
0.01M dithiothreitol (DTT)
Oligo(dT)$_{12-18}$, 250 ug/ml (Collaborative Research)
Actinomycin D, 500 ug/ml (Calibiochem)
Avian myeloblastosis virus reverse transcriptase, approximately 10,000 units/ml (obtained from Research Resources Branch, Viral Oncology Program, National Cancer Institute)

All buffers and salt solutions were autoclaved. The other solutions were prepared with sterile glass-distilled water and were stored in sterile containers. All stock solutions were stored frozen.

Procedure:

As a template for cDNA synthesis, 12S interferon mRNA from Example II was used. In order to follow the synthesis, [$\alpha$-$^{32}$P]dCTP was used, so that the cDNA could be located on polyacrylamide gels. The radioactive compound was dried by lyophilization, For each ug of mRNA, 5 uCi of [$\alpha$-$^{32}$P]dCTP at a specific activity of 400 Ci/mmol were used. The dried material was dissolved in a 2x reaction mixture consisting of 0.1M Tris.HCl, pH 8.3, 140 mM KCl, 20 mM MgCl$_2$, 1 mM dATP, 1 mM dCTP, 1 mM dGTP, 1 mM TTP, and 0.4 mM DDT. This solution was kept on ice. To this solution were added mRNA (50 ug/ml, final concentration), oligo(dT)$_{12-18}$ (25 ug/ml), actinomycin D (40 ug/ml), AMV reverse transcriptase (800 units/ml), and enough water to dilute the 2x mix to 1x. After 5 min. on ice, the reaction mixture was incubated at 46° for 10 min. Following the incubation, EDTA was added to a final concentration of 25 mM. The solution was extracted one time with an equal volume of phenol:chloroform (1/1; v/v) and the aqueous phase was chromatographed on a column of Sephadex G-100 (0.7×20 cm), equilibrated with 10 mM Tris-HCl, pH 8.0, 1 mM EDTA, 0.1M NaCl. The cDNA in the excluded volume was precipitated by addition of 0.1 volume of 2.4M sodium acetate, pH 5, and 2.5 volumes of ethanol. To remove the mRNA template, the cDNA was sedimented by centrifugation, dissolved in 0.3 ml of 0.1M NaOH, and incubated at 70° for 20 min. The solution was neutralized with 3.0 ml of 1.0M HCl and precipitated with ethanol as described above. The yield of cDNA was 10-20% of the mRNA used.

Synthesis of double-stranded cDNA from cDNA was performed with the use of DNA polymerase I (Klenow fragment), which lacked the 5'- 3' exonuclease activity. No additional primer was needed because of the 3' loop on most cDNA molecules made with AMV reverse transcriptase. In order to make ds cDNA, the 3' loop was cleaved by Aspergillus oryzae S1 nuclease.

The following stock solutions and materials were prepared:
0.5M potassium phosphate, pH 7.4
0.25M MgCl$_2$
0.1M DTT
0.05M dATP, pH 7.0
0.05M dGTP, pH 7.0
0.05M dCTP, pH 7.0
0.05M TTP, pH 7.0
[$\alpha$-$^3$H]dCTP, 22 Ci/mmol, 1 mCi/ml (Amersham)
E coli DNA polymerase I (Klenow fragment), approximately 1000 units/ml (Boehringer-Mannheim)
5x S1 nuclease buffer: 0.167M sodium acetate, pH 4.5; 5 mM ZnCl$_2$ Procedure:

To follow second strand synthesis, ten uCi of [$^3$H]dCTP (specific activity, 22 Ci/mmol) were used for each ug of mRNA used for cDNA synthesis. The dried [$^3$H]dCTP was dissolved in a 2x reaction mixture consisting of 0.2M potassium phosphate, pH 7.4, 20 mM MgCl$_2$, mM DTT, 0.4 mM each of dATP, dGTP, dCTP, and TTP. This mixture was kept on ice, cDNA in water was added, E.coli DNA polymerase I (Klenow fragment) was added to 100 units/ml, and water was added to dilute the reaction mixture to 1x. The solution was incubated overnight at 15°. After incubation, EDTA was added to 25 mM, the solution was extracted once with an equal volume of phenol:chloroform (1/1; v/v), and the aqueous phase was chromatographed on a 0.7×20 cm column of Sephadex G-100 equilibrated with 10 mM Tris.HCl, pH 8.0, 1 mM EDTA, and 0.1M NaCl. The DNA in the excluded fractions was precipitated with ethanol as described above. The yield of ds DNA was 50–100% of the amount of cDNA used as template.

At this point, the ds cDNA contained a hairpin loop. The single-stranded loop was removed by digestion with *Aspergillus oryzae* S1 nuclease, prepared by the method of Vogt, *Eur. J. Biochem.*, 33, 192 (1973). The ds cDNA was dissolved in water and 0.25 volume of 5x S1 buffer was added. An appropriate amount of S1 nuclease was added and the solution was incubated 20 min at 37°. (The amount of enzyme to be added must be determined empirically for each enzyme preparation since the activity varies from one preparation to another. This is done by measuring the decrease in TCA-precipitable counts from the ds cDNA. Usually, 50–75% of the ds cDNA is resistant to S1 nuclease. However, care must be exercised in order to avoid overdigestion due to low levels of contaminating nucleases in the S1 nuclease preparation.) The S1-digested ds cDNA was extracted once with phenol:chloroform and the aqueous phase was precipitated with ethanol as described above.

The double-stranded cDNA was layered onto a 12 ml 5 to 25% linear neutral sucrose gradient (50mM Tris, pH 7.5, 1 mM EDTA) and centrifuged in a Beckman SW40 rotor for 17 hours at 38,000 rpm (5° C.). One ml. fractions were collected, and fractions 5–9 (from the top) were pooled. (See Norgard, et al., *J. Biol. Chem.*, 255, 7665–7672 (1980)).

For the homopolymer tailing of the double-stranded cDNA, the following stock solutions and materials were prepared:

1.4M potassium cacodylate, 0.3 M Tris, pH 7.6 (pH becomes 7.2 when diluted 1:10)
15 mM $CoCl_2$
10 mM Dithiothreitol (DTT)
4 mM dCTP, pH 7.0

Procedure:

Addition of dCMP residues to the 3' ends was followed by incorporation of [$^3$H]dCTP into acid-precipitable material. Twenty-five uCi of [$^3$H]dCTP were used for each ug of mRNA used for the original cDNA synthesis. The radioactive compound was dried and redissolved in the reaction mixture. Double-stranded cDNA was dissolved in appropriate amounts of stock solutions to give final concentrations as follows: 0.14M potassium cacodylate, 0.03M Tris, pH 7.2; 1 mM DTT; 0.1 mM [$^3$H]dCTP (1 Ci/mml); 1.5 mM $CoCl_2$; and $2 \times 10^{-8}$M 3' termini. The solution without $CoCl_2$ was warmed to 37°, and the $CoCl_2$ was then added. Purified terminal deoxynucleotidyl transferase was added to a final concentration of 100 units/ml. The reaction was allowed to proceed at 37° for 5 min. At this time, a sample was taken to measure incorporation of [$^3$H]dCMP into acid-precipitable material. If tails of sufficient length had not been added, the reaction was continued by placing the solution at 37° again for the desired length of time. When tails of about 10–20 dCMP residues were generated, EDTA was added (110 mM, final concentration). The solution was extracted once with phenol:chloroform (1/1; v/v) and the aqueous phase was precipitated with ethanol. The dC-tailed ds cDNA produced by this procedure was then ready for insertion into a dG-tailed pBR322 vector as hereinafter described.

EXAMPLE V

Construction of Hybrid Plasmid

Plasmid pBR322 (Bolivar, F., et al., *Gene*, 2, 95 (1977)) (20 ug) was cut with Pst I enzyme, and approximately twenty dG residues were added to the 3' ends according to the procedure of Roychoudhury, R., et al., *Nucl. Acids Res.*, 3, 101 (1976). The reaction was conducted in a buffer consisting of 0.14M potassium cacodylate; 0.03M Tris-HCl, pH 7.0; 1 mM $CoCl_2$ and 0.01 mM dithiothreitol. The concentration of plasmid DNA 3'-hydroxyl groups was 40 nM and a 3000 molar excess of $^3$H-dGTP was employed. The reaction was catalyzed by 21 units of terminal transferase.

The dC-tailed double-stranded cDNA from Example IV was annealed to the dG-tailed pBR322 by mixing equimolar (470 n moles) of the two species in 0.9 ml of an annealing buffer composed of 10 mM Tris-HCl, pH 7.5; 100 mM NaCl and 2.5 mM $Na_2$ EDTA. This mixture was incubated for 10 minutes at 70° C. in a water bath. The bath was then transferred to a 37° C. room to allow slow cooling overnight. The next day, the bath was allowed to cool to room temperature. The resulting recombinant plasmid was used to transform *E.coli* cells.

EXAMPLE VI

Transformation

A culture of *E.coli* strain HB101 was grown overnight in 10 ml of LB medium containing 0.2% glucose. The next day, 50 ml of LB +0.2% glucose medium was inoculated with 0.5 ml of the culture, and this culture was grown at 37° C. until it had an absorbance of 0.3 at 595 nm. The culture was centrifuged in a Sorvall SS34 rotor for 10 minutes at 5000 rpm, and the resulting pellet was resuspended in 2 ml of cold 0.1M $MgCl_2$. The suspension was diluted to 25 ml with cold 0.1M $MgCl_2$ and centrifuged for 10 minutes at 3000 rpm. The cells were then resuspended in 25 ml of a solution of 0.1M $CaCl_2$ and incubated for one hour on ice. This suspension was again centrifuged for ten minutes at 3000 rpm and the cells were resuspended in 2.2 ml of the same buffer. At this point, 20 ul of the annealing mixture of Example V and 200 ul of the cell suspension were mixed together and incubated on ice for 20 minutes. The cells were then heat shocked for two minutes at 42.5° C. To the cells, 2.8 ml of LB +0.2% glucose medium was added and the mixture was incubated at 37° C. to allow expression. One hundred microliters of this mixture were added to 2.5 ml of LB medium containing 0.2% glucose and 0.8% agar, which was kept at 45° C. This "top agar" was then poured into plates containing the LB-0.2% glucose medium plus 50 ug/ml of tetracycline. These plates were incubated at 37° C. for 1–2 days until colonies appeared. (Reference: Lederberg, E., et al., *J. Bact.*, 119, 1072 (1974)).

EXAMPLE VII

Screening of Clones

Clones were screened for the presence of the alpha-interferon gene by hybridization with a synthetic radiolabeled tridecadeoxyribonucleotide probe having the following nucleotide sequence, which was known to be homologous with portions of the human beta-interferon gene and several of the known alpha-interferon genes:

C—C—T—T—C—T—G—G—A—A—C—T—G

The synthesis and use of this probe is described in copending U.S. patent application Ser. No. 286,351.

Hydridization with Probe

One ml cultures of colonies from Example VI were grown overnight in standard L-broth plus 50 ug/ml of tetracycline. Groups in ten clones were pooled and DNA was prepared by the following rapid boiling procedure: The cells were centrifuged for 10 min. at 10,000 rpm in a Sorvall SS-34 rotor. They were resuspended in 700 ul of STET buffer (8% sucrose, 5% Triton X-100, 50 mM EDTA, 50 mM Tris pH 8.0). After adding 50 ul of 10 mg/ml solution of lysozyme, the solution was immediately boiled for 40 sec. The lysate was then centrifuged at 12,000 rpm for 10 minutes at room temperature. The supernatant was carefully removed, and to it was added 150 ul of isopropanol. The DNA was precipitated for 30 minutes at $-20°$ C., centrifuged for 10 minutes at 10,000 rpm and then resuspended in 100 ul of 0.3N NaOH, 10 mM Tris (pH 8). This solution was incubated at 70° C. for 30 minutes in order to hydrolyze RNA, and was then neutralized with the addition of 10 ul of 3N HCl prior to ethanol precipitation of the DNA. The precipitated DNA was then centrifuged in an Eppendorf Microfuge for 10 minutes and the pellets were dried under vacuum. The DNA-containing pellet was dissolved in 20 ul of $H_2O$). The yield per culture was approximately 100–200 ng of DNA.

Then 10 ul of DNA was spotted directly onto S&S milliore nitrocelloulose filters (BA 85/20). In addition, 1.5 ug of SV40 DNA, which has a 10/13 base homology with the probe, and 1.5 ug of the plasmid, pBR322, were spotted as positive and negative controls, respectively. After drying, the filters were then processed by placing them sequentially at 7 minute intervals on pieces of 3 mm Whatman paper soaked with 0.5N NaOH 1.0M Tris pH7.4 (repeated once) 2XSSC buffer, (0.3M NaCl, 0.03M Na Citrate pH 7), 90% ethanol (repeated once). The filters were again dried and then baked in a vacuum oven for 2 hours at 75° C. After baking, the filters were placed in sealed plastic bags containing 10 ml of 4XSSC, 10X Denhardts buffer (0.2% bovine serum albumin, 0.2% polyvinylpyrrolidone, and 0.2% Ficoll). A preincubation step at 65° C. for 2 hours was employed to decrease nonspecific binding of radioactive probes. The solution was then removed and replaced with 4 ml of fresh 4XSSC, 10X Denhardts. The $^{32}$p-labelled probe (described in Example I) was then added ($4 \times 10^6$ cpm, specific activity $5 \times 10^8$ cpm/ug). Hybridization of the probe with the DNA bound to the filters continued overnight at 15° C. After incubation, the filters were washed 5 times with 200 ml of 4XSSC at 15° C. to remove the unhybridized probe. The filters were then dried prior to autoradiography with Kodak RP-5 film at $-80°$ C. Approximately thirty groups of clones showed some degree of hyrbridization.

Southern Blotting

Since hybridization in the initial screening was obtained with the labeled probe, the positive pools were either subdivided into individual clones or pools of 5. The DNA was prepared using the following rapid plasmid procedure: Five ml of individual clones or 10 ml of a pool of 5 clones were grown overnight in L-broth plus 50 ug/ml tetracycline. After pelleting the cells at 5000 rpm for 10 minutes, they were frozen, thawed, dissolved in 2.0 ml at 25% sucrose, 50 mM Tris pH 8, and incubated for 5 minutes at room temperature. One half of a 5 mg/ml solution of lysozyme in 10 mM Tris pH 8 was added and the solution was incubated for 5 minuts. 1.1 ml of 0.25M EDTA (pH 8) was added and the solutions were incubated for 5 minutes. The solutions were mixed with 1.5 ml of a lytic mix (2 ml 10% Triton, 10 mM Tris pH 8) (25 ml of 0.25M EDTA) (5 ml 1M Tris pH 8) (68 ml $H_2O$) and the mixture was incubated for 19 minutes at room temperature. The lysate was then centrifuged for 29 minutes at 15,000 rpm at 4° C. The supernatant was extracted with equal volumes of phenol: $CHCl_3$ prior to ethanol precipitation. The DNA was pelleted and dissolved in 400 ul $H_2O$. Approximately 20 ul was then loaded onto a 1% agarose gel (running buffer: 40 mM Tris pH 7.9, 4 mM NaOAc, 1 mM EDTA), and electrophoresed at 25 volts overnight. The DNA in the agarose gels were then transferred to nitrocellulose according to the procedure of Southern (E. M. Southern, *J. Mol Biol*, 98, 503–517 (1975)). The gel was then placed in 200 ml of 0.5M NaOH, 1.5M NaCl was 45 minutes and transferred into 200 ml of 0.5M Tris pH 7.0, 3.0M NaCl. After 45 minutes the gel was blotted with 20XSSC as the reservoir buffer. The transfer was done at room temperature overnight. After blotting the nitrocellulose filter was washed for 15 minutes in 2XSSC, then baked in a vacuum oven for 2 hours at 75° C. The prehybridization, hybridization and washings were done in the same manner as described for the initial screening. DNA from several individual clones hybridized with the probe. Restriction analysis and DNA sequencing confirmed that the procedure was effective in identifying an interferon clone which contains the gene herein designated alpha-interferon Gx-1. This clone was assigned number A3-26. A culture of the A3-26 cells was grown and analyzed for interferon activity by the viral inhibition method of Rubinstein, et al. ies (supra) and interferon activit were detected.

Substantially pure, bacterially produced human alpha-interferon Gx-1 is obtained by cultivating the A3-26 cells in large scale, under protein-expression conditions, followed by lysis of the cells and extraction and purification of the alpha-interferon Gx-1 using known techniques (e.g., see Example M of UK Patent Application GB No. 2 079 291 A, published Jan. 20, 1982).

I claim:

1. A cloned, intact human alpha-interferon Gx-1 gene, substantially free of other DNA of human origin, comprising the following deoxyribonucleotide sequence, along with the corresponding amino acid sequence for which said deoxyribonucleotide sequence codes:

```
     CYS  ASN  LEU  SER  GLN  THR  HIS
5'   TGY  AAY  YTZ  QRS  CAM  ACX  CAY

SER  LEU  ASN  ASN  ARG  ARG  THR
     QRS  YTZ  AAY  AAY  LGN  LGN  ACX

LEU  MET  ILE  MET  ALA  GLN  MET
     YTZ  ATG  ATH  ATG  GCX  CAM  ATG

GLY  ARG  ILE  SER  PRO  PHE  SER
     GGX  LGN  ATH  QRS  CCX  TTY  QRS

CYS  LEU  LYS  ASP  ARG  HIS  ASP
     TGY  YTZ  AAM  GAY  LGN  CAY  GAY
```

-continued

| | | | | | |
|---|---|---|---|---|---|
| PHE | GLY | PHE | PRO | GLN | GLU GLU |
| TTY | GGX | TTY | CCX | CAM | GAM GAM |

| PHE | ASP | GLY | ASN | GLN | PHE GLN |
|---|---|---|---|---|---|
| TTY | GAY | GGX | AAY | CAM | TTY CAM |

| LYS | ALA | GLN | ALA | ILE | SER VAL |
|---|---|---|---|---|---|
| AAM | GCX | CAM | GCX | ATH | QRS GTX |

| LEU | HIS | GLU | MET | ILE | GLN GLN |
|---|---|---|---|---|---|
| YTZ | CAY | GAM | ATG | ATH | CAM CAM |

| THR | PHE | ASN | LEU | PHE | SER THR |
|---|---|---|---|---|---|
| ACX | TTY | AAY | TYZ | TTY | QRS ACX |

| LYS | ASP | SER | SER | ALA | THR TRP |
|---|---|---|---|---|---|
| AAM | GAY | QRS | QRS | GCX | ACX TGG |

| ASP | GLU | THR | LEU | LEU | ASP LYS |
|---|---|---|---|---|---|
| GAY | GAM | ACX | YTZ | YTZ | GAY AAM |

| PHE | TYR | THR | GLU | LEU | TYR GLN |
|---|---|---|---|---|---|
| TTY | TAY | ACX | GAM | YTZ | TAY CAM |

| GLN | LEU | ASN | ASP | LEU | GLU ALA |
|---|---|---|---|---|---|
| CAM | YTZ | AAY | GAY | YTZ | GAM GCX |

| CYS | MET | MET | GLN | GLU | VAL GLY |
|---|---|---|---|---|---|
| TGY | ATG | ATG | CAM | GAM | GTX GGX |

| VAL | GLU | ASP | THR | PRO | LEU MET |
|---|---|---|---|---|---|
| GTX | GAM | GAY | ACX | CCX | YTZ ATG |

| ASN | VAL | ASP | SER | ILE | LEU THR |
|---|---|---|---|---|---|
| AAY | GTX | GAY | QRS | ATH | YTZ ACX |

| VAL | ARG | LYS | TYR | PHE | GLN ARG |
|---|---|---|---|---|---|
| GTX | LGN | AAM | TAY | TTY | CAM LGN |

| ILE | THR | LEU | TYR | LEU | THR GLU |
|---|---|---|---|---|---|
| ATH | ACX | YTZ | TAY | YTZ | ACX GAM |

| LYS | LYS | TYR | SER | PRO | CYS ALA |
|---|---|---|---|---|---|
| AAM | AAM | TAY | QRS | CCX | TGY GCX |

| TRP | GLU | VAL | VAL | ARG | ALA GLU |
|---|---|---|---|---|---|
| TGG | GAM | GTX | GTX | LGN | GCX GAM |

| ILE | MET | ARG | SER | PHE | SER LEU |
|---|---|---|---|---|---|
| ATH | ATG | LGN | QRS | TTY | QRS YTZ |

| SER | ALA | ASN | LEU | GLN | GLU ARG |
|---|---|---|---|---|---|
| QRS | GCX | AAY | YTZ | CAM | GAM LGN |

| LEU | ARG | ARG | LYS | GLU | |
|---|---|---|---|---|---|
| YTZ | LGN | LGN | AAM | GAM | 3' | wherein the 5' to 3' strand, beginning with the amino terminus and the amino acids for which each triplet codes are shown, and wherein A is deoxyadenyl
T is thymidyl
G is deoxyguanyl
C is deoxycytosyl
X is A, T, C or G
Y is T or C
when Y is C, Z is A, T, C or G
when Y is T, Z is A or G
H is A, T or C
Q is T or A
when Q is T, R is C and S is A, T, C or G
When Q is A, R is G and S is T or C
M is A or G
L is A or C
when L is A, N is A or G
when L is C, N is A, T, C or G
GLY is glycine
ALA is alanine
VAL is valine
LEU is leucine
ILE is isoleucine
SER is serine
THR is threonine
PHE is phenylalanine
TYR is tyrosine
TRP is tryptophan
CYS is cysteine
MET is methionine
ASP is aspartic acid
GLU is glutamic acid
LYS is lysine
ARG is arginine
HIS is histidine
PRO is proline
GLN is glutamine
ASN is asparagine.

2. The alpha-interferon Gx-1 gene of claim 1, wherein deoxyribonucleotide sequence is:

| CYS | ASN | LEU | SER | GLN | THR |
|---|---|---|---|---|---|
| TGT | AAT CTG | TCT | CAA | ACC | |

| HIS | SER | LEU | ASN | ASN | ARG |
|---|---|---|---|---|---|
| CAC | AGC | CTG | AAT | AAC | AGG |

| ARG | THR | LEU | MET | ILE | MET |
|---|---|---|---|---|---|
| AGG | ACT | TTG | ATG | ATA | ATG |

| ALA | GLN | MET | GLY | ARG | ILE |
|---|---|---|---|---|---|
| GCA | CAA | ATG | GGA | AGA | ATC |

| SER | PRO | PHE | SER | CYS | LEU |
|---|---|---|---|---|---|
| TCT | CCT | TTC | TCC | TGC | CTG |

| LYS | ASP | ARG | HIS | ASP | PHE |
|---|---|---|---|---|---|
| AAG | GAC | AGA | CAT | GAC | TTT |

| GLY | PHE | PRO | GLN | GLU | GLU |
|---|---|---|---|---|---|
| GGA | TTT | CCT | CAG | GAG | GAG |

| PHE | ASP | GLY | ASN | GLN | PHE |
|---|---|---|---|---|---|
| TTT | GAT | GGC | AAC | CAG | TTC |

| GLN | LYS | ALA | GLN | ALA | ILE |
|---|---|---|---|---|---|
| CAG | AAG | GCT | CAA | GCC | ATC |

| SER | VAL | LEU | HIS | GLU | MET |
|---|---|---|---|---|---|
| TCT | GTC | CTC | CAT | GAG | ATG |

| ILE | GLN | GLN | THR | PHE | ASN |
|---|---|---|---|---|---|
| ATC | CAG | CAG | ACC | TTC | AAT |

| LEU | PHE | SER | THR | LYS | ASP |
|---|---|---|---|---|---|
| CTC | TTC | AGC | ACA | AAG | GAC |

| SER | SER | ALA | THR | TRP | ASP |
|---|---|---|---|---|---|
| TCA | TCT | GCT | ACT | TGG | GAT |

```
GLU THR LEU LEU ASP LYS
G A G A C A C T T C T A G A C A A A

PHE TYR THR GLU LEU TYR
T T C T A C A C T G A A C T T T A C

GLN GLN LEU ASN ASP LEU
C A G C A G C T G A A T G A C C T G

GLU ALA CYS MET MET GLN
G A A G C C T G T A T G A T G C A G

GLU VAL GLY VAL GLU ASP
G A G G T T G G A G T G G A A G A C

THR PRO LEU MET ASN VAL
A C T C C T C T G A T G A A T G T G

ASP SER ILE LEU THR VAL
G A C T C T A T C C T G A C T G T G

ARG LYS TYR PHE GLN ARG
A G A A A A T A C T T T C A A A G A

ILE THR LEU TYR LEU THR
A T C A C C C T C T A T C T G A C A

GLU LYS LYS TYR SER PRO
G A G A A G A A A T A C A G C C C T

CYS ALA TRP GLU VAL VAL
T G T G C A T G G G A G G T T G T C

ARG ALA GLU ILE MET ARG
A G A G C A G A A A T C A T G A G A

SER PHE SER LEU SER ALA
T C C T T C T C T T T A T C A G C A

ASN LEU GLN GLU ARG LEU
A A C T T G C A A G A A A G A T T A

ARG ARG LYS GLU
        A G G A G G A A G G A A.
```

3. The alpha-interferon Gx-1 gene of claim 1, wherein the deoxyribonucleotide sequence is:

```
MET MET ALA LEU VAL VAL
A T G A T G G C C C T G G T G G T G

LEU SER CYS LYS SER SER
   C T C A G C T G C A A G T C A A G C

CYS SER LEU GLY CYS ASN
   T G C T C T C T G G G C T G T A A T

LEU SER GLN THR HIS SER
   C T G T C T C A A A C C C A C A G C

LEU ASN ASN ARG ARG THR
   C T G A A T A A C A G G A G G A C T

LEU MET ILE MET ALA GLN
   T T G A T G A T A T G G C A C A A A

MET GLY ARG ILE SER PRO
   T G G G A A G A A T C T C T C C T

PHE SER CYS LEU LYS ASP
   T T C T C C T G C C T G A A G G A C

ARG HIS ASP PHE GLY PHE
   A G A C A T G A C T T T G G A T T T

PRO GLN GLU GLU PHE ASP
   C C T C A G G A G G A G T T T G A T

GLY ASN GLN PHE GLN LYS
   G G C A A C C A G T T C C A G A A G
```

```
ALA GLN ALA ILE SER VAL
G C T C A A G C C A T C T C T G T C

LEU HIS GLU MET ILE GLN
C T C C A T G A G A T G A T C C A G

GLN THR PHE ASN LEU PHE
C A G A C C T T C A A T C T C T T C

SER THR LYS ASP SER SER
A G C A C A A A G G A C T C A T C T

ALA THR TRP ASP GLU THR
G C T A C T T G G G A T G A G A C A

LEU LEU ASP LYS PHE TYR
C T T C T A G A C A A A T T C T A C

THR GLU LEU TYR GLN GLN
A C T G A A C T T T A C C A G C A G

LEU ASN ASP LEU GLU ALA
C T G A A T G A C C T G G A A G C C

CYS MET MET GLN GLU VAL
T G T A T G A T G C A G G A G G T T

GLY VAL GLU ASP THR PRO
G G A G T G G A A G A C A C T C C T

LEU MET ASN VAL ASP SER
C T G A T G A A T G T G G A C T C T

ILE LEU THR VAL ARG LYS
A T C C T G A C T G T G A G A A A A

TYR PHE GLN ARG ILE THR
T A C T T T C A A A G A A T C A C C

LEU TYR LEU THR GLU LYS
C T C T A T C T G A C A G A G A A G

LYS TYR SER PRO CYS ALA
A A A T A C A G C C C T T G T G C A

TRP GLU VAL VAL ARG ALA
T G G G A G G T T G T C A G A G C A

GLU ILE MET ARG SER PHE
G A A A T C A T G A G A T C C T T C

SER LEU SER ALA ASN LEU
T C T T T A T C A G C A A A C T T G

GLN GLU ARG LEU ARG ARG
C A A G A A A G A T T A A G G A G G

LYS GLU
                      A A G G A A.
```

4. The alpha-interferon Gx-1 gene of claim 1, wherein the deoxyribonucleotide sequence is:

```
C A G A A A A C C T A C C C A A G
   G A G T G T T A C C C C T C A T C
   A A C C A G C C C A G C A G C A T
   C T T C G G G A T T C C C A A T G
   C A T T G C C C T T T G C T T T A

MET MET ALA LEU VAL VAL
   A T G A T G G C C C T G G T G G T G

LEU SER CYS LYS SER SER
   C T C A G C T G C A A G T C A A G C

CYS SER LEU GLY CYS ASN
   T G C T C T C T G G G C T G T A A T

LEU SER GLN THR HIS SER
   C T G T C T C A A A C C C A C A G C
```

-continued

| LEU | ASN | ASN | ARG | ARG | THR |
|---|---|---|---|---|---|
| C T G | A A T | A A C | A G G | A G G | A C T |

| LEU | MET | ILE | MET | ALA | GLN |
|---|---|---|---|---|---|
| T T G | A T G | A T A | A T G | G C A | C A A |

| MET | GLY | ARG | ILE | SER | PRO |
|---|---|---|---|---|---|
| A T G | G G A | A G A | A T C | T C T | C C T |

| PHE | SER | CYS | LEU | LYS | ASP |
|---|---|---|---|---|---|
| T T C | T C C | T G C | C T G | A A G | G A C |

| ARG | HIS | ASP | PHE | GLY | PHE |
|---|---|---|---|---|---|
| A G A | C A T | G A C | T T T | G G A | T T T |

| PRO | GLN | GLU | GLU | PHE | ASP |
|---|---|---|---|---|---|
| C C T | C A G | G A G | G A G | T T T | G A T |

| GLY | ASN | GLN | PHE | GLN | LYS |
|---|---|---|---|---|---|
| G G C | A A C | C A G | T T C | C A G | A A G |

| ALA | GLN | ALA | ILE | SER | VAL |
|---|---|---|---|---|---|
| G C T | C A A | G C C | A T C | T C T | G T C |

| LEU | HIS | GLU | MET | ILE | GLN |
|---|---|---|---|---|---|
| C T C | C A T | G A G | A T G | A T C | C A G |

| GLN | THR | PHE | ASN | LEU | PHE |
|---|---|---|---|---|---|
| C A G | A C C | T T C | A A T | C T C | T T C |

| SER | THR | LYS | ASP | SER | SER |
|---|---|---|---|---|---|
| A G C | A C A | A A G | G A C | T C A | T C T |

| ALA | THR | TRP | ASP | GLU | THR |
|---|---|---|---|---|---|
| G C T | A G T | T G G | G A T | G A G | A C A |

| LEU | LEU | ASP | LYS | PHE | TYR |
|---|---|---|---|---|---|
| C T T | C T A | G A C | A A A | T T C | T A C |

| THR | GLU | LEU | TYR | GLN | GLN |
|---|---|---|---|---|---|
| A C T | G A A | C T T | T A C | C A G | C A G |

| LEU | ASN | ASP | LEU | GLU | ALA |
|---|---|---|---|---|---|
| C T G | A A T | G A C | C T G | G A A | G C C |

| CYS | MET | MET | GLN | GLU | VAL |
|---|---|---|---|---|---|
| T G T | A T G | A T G | C A G | G A G | G T T |

| GLY | VAL | GLU | ASP | THR | PRO |
|---|---|---|---|---|---|
| G G A | G T G | G A A | G A C | A C T | C C T |

| LEU | MET | ASN | VAL | ASP | SER |
|---|---|---|---|---|---|
| C T G | A T G | A A T | G T G | G A C | T C T |

| ILE | LEU | THR | VAL | ARG | LYS |
|---|---|---|---|---|---|
| A T C | C T G | A C T | G T G | A G A | A A A |

| TYR | PHE | GLN | ARG | ILE | THR |
|---|---|---|---|---|---|
| T A C | T T T | C A A | A G A | A T C | A C C |

| LEU | TYR | LEU | THR | GLU | LYS |
|---|---|---|---|---|---|
| C T C | T A T | C T G | A C A | G A G | A A G |

| LYS | TYR | SER | PRO | CYS | ALA |
|---|---|---|---|---|---|
| A A A | T A C | A G C | C C T | T G T | G C A |

| TRP | GLU | VAL | VAL | ARG | ALA |
|---|---|---|---|---|---|
| T G G | G A G | G T T | G T C | A G A | G C A |

| GLU | ILE | MET | ARG | SER | PHE |
|---|---|---|---|---|---|
| G A A | A T C | A T G | A G A | T C C | T T C |

| SER | LEU | SER | ALA | ASN | LEU |
|---|---|---|---|---|---|
| T C T | T T A | T C A | G C A | A A C | T T G |

| GLN | GLU | ARG | LEU | ARG | ARG |
|---|---|---|---|---|---|
| C A A | G A A | A G A | T T A | A G G | A G G |

| LYS | GLU | | | | |
|---|---|---|---|---|---|
| A A G | G A A | T G A | A A A | C T G | G T |

T C A A C A T C G A A A T G A T T
C T C A T T G A C T A G T A C A C

-continued
C A T T T C A C A C T T C T T G A
G T T C T G C C G T T T C A A A T
A T T A A T T T C T G C T A T A T
C C A T G A C T T G A G T T G A A
T C A A A T T T T C A A A C G T
T T C A C A C G T G T T A A G C A
A C A C T T C T T T A G C C T C C A
C A G G G A C A A A A T C T T T A
C A G A T G A T C A T G C C A A T
C T A T C T A T T C T A T C T A T
T T A T C T A T C T G T C T G T C
T T C T A T C T A A T C T A T T T
A A A T A T T T A T T T A T T T A
T A A G A T T T A A A T T A T T T
T A A A C T T A T G T T T G T T C
A G G T A A T A T T A C A T C C A
C C T T T A C T T T G T G G C T A
A T A T A A T A A A A T A T G T T
C T T T A T G T T T T G T C A A G
C T G A T T A T T T T G C T T T G
T T A C T T A G A T T T T T A G.

5. A plasmid having the capability of replication in a procaryotic organsm, comprising the alpha-inteferon Gx-1 gene of claim 2, 3 or 4.

6. The plasmid of claim 5, further comprising promoter, operator and translation initiation sequences which are capable of directing transcription and translation of the deoxyribonucleotide sequence coding for human alpha-interferon Gx-1 in a procaryotic organism.

7. The plasmid of claim 5, wherein said procaryotic organism is of the genus Escherichia.

8. The plasmid of claim 6, wherein the promoter, operator and translation initiation sequences are capable of directing transcription and translation in a bacterium of the genus Escheria.

9. The plasmid of claim 8, wherein the promoter, operator and translation initiation sequences are derived from the lac or trp operon of *Escherichia coli*.

10. A microroganism transformed by the plasmid of claim 5.

11. The microorganism of claim 10, of the genus Escherichia.

12. The microorganism of claim 11, of the species *coli*.

13. A plasmid having the capability of replication in a unicellular procaryotic or eucaryotic organism, comprising a deoxynucleotide sequence coding for human alpha-interferon Gx-1.

14. The plasmid of claim 13, further comprising promoter, operator and translation initiation sequences which are capable of directing transcription and the translation of the deoxyribonucleotide sequence coding for human alpha-interferon Gx-1 in a procaryotic organism.

15. A microorganism transformed by the plasmid of claim 13 or 14.

16. A microorganism of the genus and species of *Escherichia coli* designated as A3-26 and deposited with the American Type Culture Collection as ATOO No. 39063.

17. A method for producing substantially pure human alpha-1interferon Gx-1, which comprises cultivating on an aqueous nutrient medium containing assimilable sources of carbon, nitrogen and essential minerals, under alpha-interferon Gx-1 procaryotic organism transformed by a plasmid capable of replicating in said organism and having a deoxynucleotide sequence coding for human alpha-interferon Gx-1; and recovering the alpha-interferon Gx-1 so produced.

18. The method of claim 16, wherein the procaryotic organism is *Escherichia coli*.

19. The method of claim 18, wherein said procaryotic organism is strain A3-26.

* * * * *

UNITED STATES PATENT AND TRADEMARK OFFICE
CERTIFICATE OF CORRECTION

PATENT NO. : 4,695,543
DATED : September 22, 1987
INVENTOR(S) : Sloma

It is certified that error appears in the above-identified patent and that said Letters Patent is hereby corrected as shown below:

Column 2, line 18, "Alha-interferons" should be "Alpha-interferons"

Column 3, line 19, "effeted," should be "effected,"

Column 4, line 25, "0 35" should be deleted.

Signed and Sealed this

Twenty-sixth Day of April, 1988

Attest:

DONALD J. QUIGG

Attesting Officer     Commissioner of Patents and Trademarks